United States Patent
Hibst et al.

(10) Patent No.: US 6,186,780 B1
(45) Date of Patent: Feb. 13, 2001

(54) METHOD AND DEVICE FOR THE RECOGNITION OF CARIES, PLAQUE, CONCRETIONS OR BACTERIAL INFECTION ON TEETH

(75) Inventors: Raimund Hibst, Erbach; Robert Paulus, Gersthofen, both of (DE)

(73) Assignee: Kaltenbach & Voigt GmbH & Co., Biberach/Riss (DE)

(*) Notice: Under 35 U.S.C. 154(b), the term of this patent shall be extended for 0 days.

(21) Appl. No.: 09/309,867

(22) Filed: May 11, 1999

(30) Foreign Application Priority Data

Jun. 4, 1998 (DE) ............................................. 198 25 021

(51) Int. Cl.⁷ .................................................... A61C 1/00
(52) U.S. Cl. ............................................. 433/29; 433/215
(58) Field of Search ........................... 433/29, 215, 229; 600/317; 356/303, 317, 318

(56) References Cited

U.S. PATENT DOCUMENTS

| | | | |
|---|---|---|---|
| 4,184,175 | * 1/1980 | Mullane, Jr. | 433/29 |
| 4,479,499 | * 10/1984 | Alfano | 433/29 |
| 5,074,306 | * 12/1991 | Green et al. | 600/317 |
| 5,306,144 | * 4/1994 | Hibst et al. | 433/29 |
| 5,382,163 | * 1/1995 | Putnam | 433/215 |
| 5,400,791 | * 3/1995 | Schier et al. | 600/317 |
| 5,460,971 | * 10/1995 | Gottlieb | 600/317 |
| 5,880,826 | * 3/1999 | Jung et al. | 433/29 |
| 5,894,620 | * 4/1999 | Polaert et al. | 433/215 |
| 6,024,562 | * 2/2000 | Hibst et al. | 433/29 |
| 6,053,731 | * 4/2000 | Heckenberger | 433/29 |

* cited by examiner

Primary Examiner—Todd E. Manahan
(74) Attorney, Agent, or Firm—Scully, Scott, Murphy & Presser (57) ABSTRACT

Method and device for the recognition of caries, plaque, concretions or bacterial infections on teeth, whereby with the aid of a light source (1) an excitation radiation (9) is generated which is directed at a tooth (4) to be investigated and there brings about a fluorescence radiation (10). The fluorescence radiation is detected and evaluated with a detection device (8). A spectral filter is arranged before the detection device (8) which restricts the fluorescence radiation detected and evaluated by the detection device (8) to wavelengths greater than ca. 800 nm, in order to make possible an improved detection of carious tooth regions. Advantageously, the irradiation of the tooth to be investigated is effected with a relatively long wavelength excitation radiation (9), the wavelength of which may be for example ca. 780 nm.

18 Claims, 9 Drawing Sheets

| Excitation wavelength | 655nm (P=0,6mW) | | | | | 780nm (P=3,3mW) | | | |
|---|---|---|---|---|---|---|---|---|---|
| Passband of filter | >670nm | >850nm | | | | >850nm | | | |
| Amplification factor | 50 | 50 | | 100 | | 50 | | 100 | |
| Probe type | A | A | B | A | B | A | B | A | B |
| Tooth enamel (S) | 1,63 | 0,01 | 0,01 | 0,01 | 0,01 | 0,01 | 0,01 | 0,05 | 0,04 |
| Dentin | -- | 0,01 | 0,01 | 0,02 | 0,01 | 0,01 | 0,01 | 0,12 | 0,10 |
| Caries (K) | 10,63 | 0,65 | 0,52 | 1,35 | 0,92 | 2,18 | 3,10 | 5,70 | 7,20 |
| Caries/ Tooth enamel(K/S) | 12,6 | 65 | 52 | 135 | 92 | 218 | 310 | 114 | 180 |

Fig. 10a

| Excitation wavelength | 655nm | | | | | 780nm | | |
|---|---|---|---|---|---|---|---|---|
| Passband of filter | >670nm | | >850nm | | | >850nm | | |
| Tooth | A | C | A | B | C | A | B | C |
| Tooth enamel (S) | 10,9 | 2,7 | 0,6 | >0,01 | >0,01 | 0,04 | >0,01 | >0,01 |
| Caries (K) | 78,7 | 34,4 | 8,8 | 0,9 | 1,1 | 28,4 | 0,7 | 0,94 |
| | | | | | | | | |
| K/S | 7,2 | 12,7 | 14,7 | >90 | >108 | 710 | >70 | >94 |

METHOD AND DEVICE FOR THE RECOGNITION OF CARIES, PLAQUE, CONCRETIONS OR BACTERIAL INFECTION ON TEETH

The present invention relates to a method and to a corresponding device for the recognition of caries, plaque, concretions, bacterial infection etc. on teeth in accordance with the preamble of claim 1 or 8.

It is known to identify caries, plaque or bacterial infection on teeth through visual investigation or through employment of X-rays. However, with the aid of a visual investigation, satisfactory results frequently cannot be attained since, for example, caries in the early stage or at a difficult to observe tooth region cannot be identified. Although, on the other hand, X-rays have proved to be a very effective way of identifying an incidence of caries or other tooth diseases, this investigation method is also not optimal due to the damaging effect of the X-rays for human health. There was thus the need to develop a new technique in order to be able to identify the presence of caries on teeth.

In DE 3031249 C2 there was proposed a contactless investigation method for the identification of caries on human teeth, whereby the tooth is irradiated with practically monochromatic light. The practically monochromatic light radiation excites a fluorescence radiation at the tooth. Thereby it was discovered that the fluorescence spectrum reflected from the tooth manifests significant differences between carious and healthy tooth regions. Thus, in the red spectral range of the fluorescence spectrum of the tooth (i.e. between 550 nm and 650 nm) the intensity is significantly higher than with a healthy tooth. In contrast, in the blue spectral range of the reflected fluorescence spectrum of the tooth (i.e. between 350 nm and 450 nm) the intensity of the fluorescence radiation for carious regions and healthy regions of the tooth is virtually identical. In DE 3031249 C2 it was therefore proposed to irradiate the tooth with a wavelength of 410 nm and, by means of two filters, to detect the fluorescence radiation of the tooth for a first wavelength of 450 nm and a second wavelength of 610 nm, i.e. in the blue and red spectral region, for example with the aid of photodetectors. The fluorescence radiation intensities detected by means of this arrangement are subtracted so that on the basis of the thus obtained difference intensity a healthy tooth region can be unambiguously distinguished from a carious tooth region.

DE 4200741 A1 proposes, as an advantageous further development, to bring about the fluorescence of the tooth by means of an excitation radiation having a wavelength in the range 360 nm to 580 nm and to filter out the fluorescence radiation brought about at the irradiated tooth in the wavelength range between 620 nm and 720 nm. By means of this measure it is achieved that the spacing between the wavelength of the excitation radiation and of the received fluorescence radiation is sufficiently great such that the excitation radiation cannot corrupt the evaluation results through superposition on the fluorescence radiation.

The above-described known investigation methods or devices have in common that for the excitation of the fluorescence at a tooth to be investigated an excitation radiation having a relatively short wavelength, i.e. smaller than 580 nm, is employed. Thereby, although on the one hand a relatively greater effective cross-section for the generation of the fluorescence radiation is attained, however the fluorescence radiation for healthy tooth tissue is significantly stronger than that for carious lesions. Therefore, with the above-described investigation methods an elaborate direct comparison of the fluorescence radiation emitted in a particular wavelength range from neighbouring healthy and carious regions is necessary, or the measurement signals of the detected fluorescence radiation in two different wavelength ranges must be compared with one another in an elaborate manner.

In DE 19541686 A1, which like DE 4200741 A1 originates from the applicant of the present application, it was therefore proposed to employ for the excitation of the fluorescence at a tooth to be investigated an excitation radiation having a wavelength between 600 nm and 670 nm. For the detection of the fluorescence radiation excited at the irradiated tooth, a spectral filter arrangement is employed which lets through fluorescence radiation having a wavelength between 670 nm and 800 nm, i.e. in accordance with DE 19541686 A1 only fluorescence radiation having a wavelength between 670 nm and 800 nm is evaluated for the recognition of caries, plaque or bacterial infection at the irradiated tooth.

With the aid of the measures proposed in DE 19541686 A1 an improved sensitivity of the caries detection is attained. The excitation of the fluorescence radiation with an excitation radiation in the above-mentioned wavelength range between 600 nm and 670 nm has the advantage that the fluorescence radiation from healthy tooth regions strongly reduces with such excitation wavelengths, so that the fluorescence radiation from carious regions is only slightly superposed with the autofluorescence of the healthy tooth tissue and caries, plaque or bacterial infection of teeth can be recognised simply, in a manner not prone to disruption and with high sensitivity.

Starting from the above described state of the art the present invention has the object of further increasing the detection sensitivity in the recognition of caries, plaque, concretions or bacterial infection on teeth, i.e. to increase the difference between measurement signals from healthy tooth regions on the one hand and carious tooth regions on the other hand.

In accordance with the present invention this object is achieved by means of a method having the features of claim 1 or a device having the features of claim 8. The subclaims describe preferred and advantageous embodiments of the present invention, which for their part contribute to an improved sensitivity or to a construction of the device in accordance with the invention which is as simple as possible.

In accordance with the present invention it is proposed, for the recognition of caries, plaque, concretions, bacterial infection etc., to evaluate fluorescence radiation having a wavelength above ca. 800 nm. In accordance with the knowledge on which the present patent application is based, with the aid of this measure there can be attained a particularly sensitive recognition of hidden caries (for example in fissures or approximal tooth regions), since in this wavelength range of the fluorescence radiation the proportion of caries specific fluorophores and other deposits is particularly high, but healthy tooth enamel or dentine does not fluoresce or fluoresces only very slightly.

The fluorescence radiation can in principal be excited with all wavelengths below 800 nm. With regard to the optical penetration depth an excitation with radiation of as long a wavelength as possible is advantageous, due to the scattering which reduces with increasing wavelength, so that in accordance with a preferred exemplary embodiment the excitation wavelength lies between 680 nm and 800 nm, in particular between 700 nm and 800 nm, and preferably is 780 nm.

In the development of the present invention it has been revealed that evidently above and below a particular excitation wavelength different groups of fluorophores are detected, so that for a differentiation (e.g. of decalcifications and lesions having organic deposits or bacterial infection) the combination of different detection ranges, i.e. of different evaluated wavelength ranges of the fluorescence radiation, and/or of excitation wavelengths, is also advantageous.

The present invention will be described in more detail below with reference to preferred exemplary embodiments and with reference to the accompanying drawings.

Figure 1:
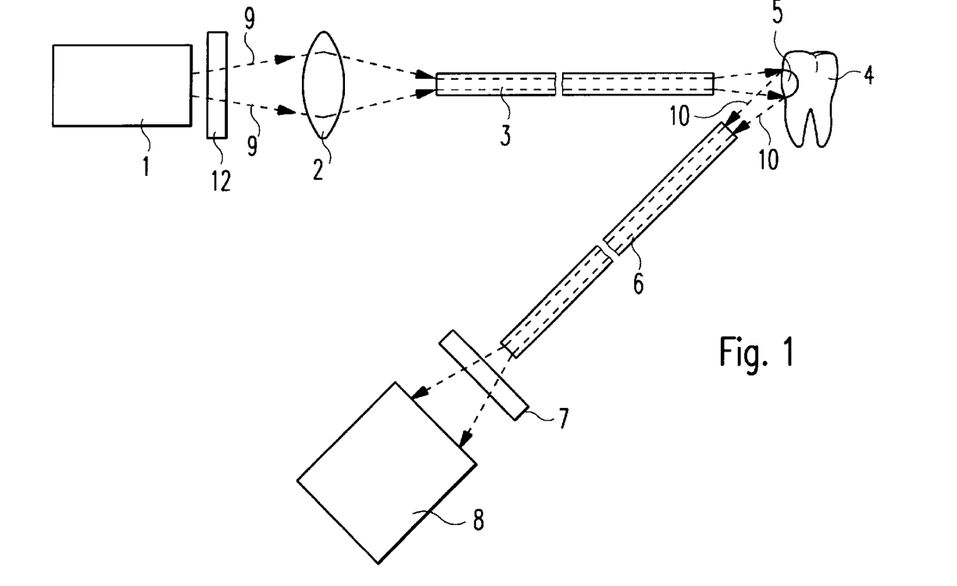
FIG. 1 shows a first exemplary embodiment of the device in accordance with the invention for the recognition of caries, plaque, concretions or bacterial infection on teeth.

FIG. 1 shows a first exemplary embodiment of a device in accordance with the invention for the recognition of caries, plaque, concretions or bacterial infection on teeth. A light source 1 generates an excitation radiation 9 which, via a coupling lens system 2 and a light conductor, is delivered to a region 5 of a tooth 4 to be investigated. The excitation radiation lies for example between 680 nm and 800 nm and is preferably ca. 780 nm. Through the excitation radiation there is brought about at the irradiated tooth region 5 a fluorescence radiation 10 over a relatively wide spectral region which, via a second light conductor 6 and a spectral filter 7, is delivered to a detection device 8 for the detection and evaluation of the fluorescence radiation of the tooth. The spectral filter is so configured that it is transparent only for a fluorescence radiation having a wavelength greater than ca. 800 nm. Preferably, the limit frequency of the spectral filter lies at ca. 850 nm. The detection device 8 directly evaluates the fluorescence radiation 10 delivered thereto and determines directly from the detected fluorescence radiation 10 the presence or non-presence of caries, plaque or bacterial infection at the irradiated tooth region 5.

The light source 1 is preferably HeNe laser or a laser diode which generates excitation radiation in the above-described preferred wavelength range.

Investigations have shown that the laser diodes serving and tested as light source 1 emit, in addition to the respective laser line, also a background of long wavelength radiation, whereby this long wavelength radiation passes through the spectral filter 7 arranged before the detection device 8, together with the fluorescence radiation actually to be detected, and thus can corrupt the measurement. This long wavelength background radiation can be eliminated with the aid of a high-pass filter arranged after the light source or laser diode 1 the cut-off wavelength of which, defining its pass band, advantageously lies between the actual excitation wavelength of the laser diode or light source 1 and the short wavelength end of the respectively selected detection window, such that the excitation radiation 9 can pass unhindered through the high-pass filter 12 but the long wavelength background radiation is reliably filtered out over the entire spectral range of the detected fluorescence radiation.

The excitation radiation 9 passing through the high-pass filter 12 is coupled into the light conductor 3 via a separate lens system 2 or via collimator optics frequently already integrated in the case of laser diodes. Such a light conductor may be rigid or flexible and additionally at its end towards the tooth may be equipped with further optical means (lenses) for aimed beam guiding and/or may be adapted in its dimensions to the mouth region of the patient and to the tooth to be investigated. Further, there may be mounted on or in the light conductor 3 exchangeable deflection mirrors or lenses, which facilitate an investigation of the tooth 4. The employment of the light conductor 3 thus makes it possible to deliver the excitation radiation 9 in an aimed manner to the region 5 of the tooth to be investigated or to the tooth 4. Thereby, the device in accordance with the invention can be flexibly adapted to various requirements in daily practice in the recognition of caries on teeth of a patient. What has been said with regard to the light conductor 3 applies to the same extent also for the further light conductor 6 which delivers the fluorescence radiation to the spectral filter 7. The two light conductors 3 and 6 may in each case have a plurality of light conductor fibres. With the employment of a laser as light source 1, the excitation radiation 9 and the fluorescence radiation 10 can be transmitted via relatively thin light conductor fibres having a core diameter of for example 200 μm. The employment of two separate light conductors 3 and 6 for the transmission of the excitation radiation 9 and the fluorescence radiation 10 is advantageous in particular for the investigation of exterior surfaces of a tooth. With the exemplary embodiment illustrated in FIG. 1 the positions of the light conductors 3 and 6 can thus be selected independently of one another and individually at the tooth, which in the individual case makes possible an optimisation of the detection sensitivity for deep lying or very hidden lesions.

The spectral filter 7 of the device in accordance with the invention may be realised by means of a coloured glass cut-off filter or other optical elements for spectral selection, e.g. a diffraction grating, spectrometer, etc. The filter is advantageously so configured that it itself fluoresces as little as possible.

The detection device 8 has advantageously as light sensitive elements photodiodes for the detection of the fluorescence radiation. For increasing the sensitivity, the photodiodes may be equipped with an integrated preamplifier. Likewise, a photomultiplier may be considered as amplifier element in the optical field of the fluorescence radiation 10.

For the case that both the light source 1 and also the light sensitive element of the detection device 8 consist of semiconductor components, there can be employed for the voltage supply of the device in accordance with the invention a low voltage mains unit which because of the slight power take-up might consist solely of batteries or accumulators.

Figure 2:
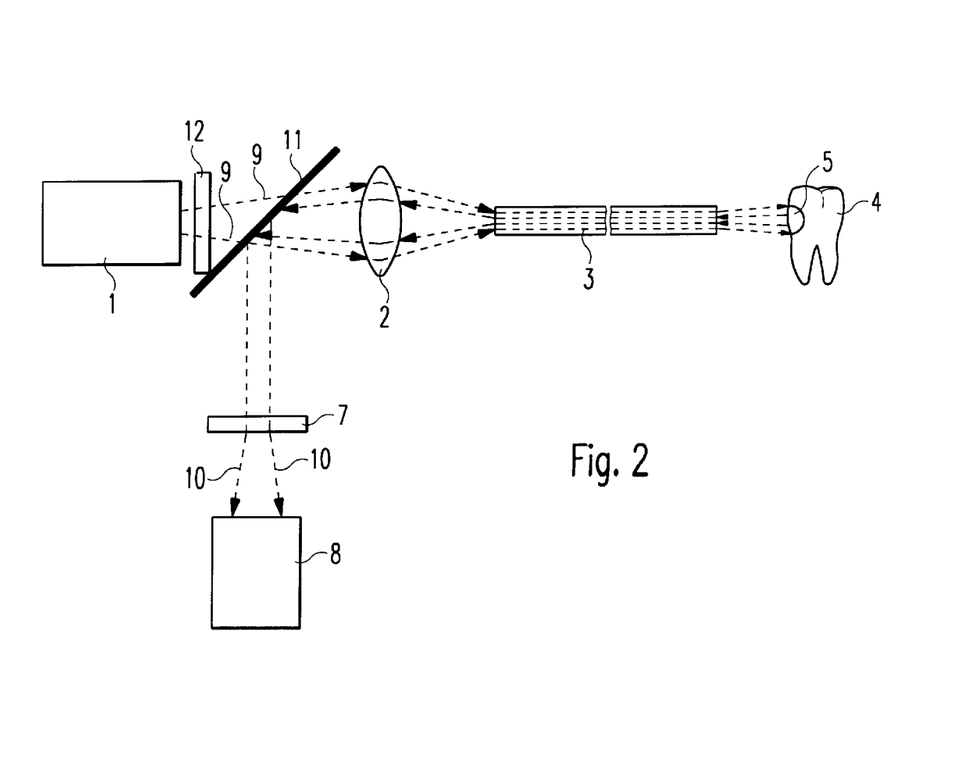
FIG. 2 shows a second exemplary embodiment of the device in accordance with the invention.

FIG. 2 shows a second exemplary embodiment of a device in accordance with the invention for the recognition of caries, plaque or bacterial infection, whereby the components of the device already illustrated in FIG. 1 are provided with identical reference signs. In the exemplary embodiment illustrated in FIG. 2, the fluorescence radiation 10 is transmitted via the same light conductor as the excitation radiation 9. For coupling the fluorescence radiation 10 out of the beam path in the light conductor 3 there is provided a beam divider 11, which is arranged between the light source 1 and the lens arrangement 2 or alternatively between the lens arrangement 2 and the end of the light conductor 3 towards the light source. This configuration of the present invention is of particularly significance for use for the investigation of root canals.

The excitation radiation 9 and the fluorescence radiation 10 may—as has already been explained with reference to the exemplary embodiment illustrated in FIG. 1—be transmitted in each case via a plurality of light conductor fibres of the light conductor 3. In order to increase or stabilize the reliability and precision of detection, in this case the light conductor 3 may include one or more centrally arranged light conductor fibres for the transmission of the excitation radiation 9 and a plurality of light conductor fibres for the transmission of the fluorescence radiation 10 arranged concentrically around this or these central light conductor fibre(s). At the end of the light conductor fibre 3 towards the detection device 8, the detection fibres—which transmit the fluorescence radiation excited at the tooth 4—may be bundled for improvement of the detection accuracy. By means of chamfering of the outer light conductor fibres, which are provided for the transmission of the fluorescence radiation 10, there can further be attained a reliable and extensive overlapping of the excitation radiation 9 and the fluorescence radiation 10, which contributes to a further improvement of the detection accuracy.

With the two exemplary embodiments illustrated in FIGS. 1 and 2, the detection device 8 may be coupled with a (not shown) display device which visually represents the measurement signal delivered from the detection device 8. Likewise, an acoustic indication of the measurement signal is conceivable.

Investigations have revealed that in particular light conductors of plastics or glass can fluoresce in the spectral range employed in accordance with the present invention (with the relatively expensive quartz light conductors, in contrast, the fluorescence radiation is comparatively slight). This has the consequence that both in the excitation fibre and also in the detection fibre fluorescence radiation can be brought about which together with the fluorescence radiation brought about at the tooth can pass through the spectral filter 7 and thus corrupt the measurement results. In particular with reflecting surfaces the fluorescence signal generated by the fibres themselves can become a significant disturbing factor which is to be avoided.

In order to overcome this problem there may be employed—as has already been mentioned above—non-fluorescing light conductors, preferably of quartz. Since, however, these light conductors are very expensive this alternative comes into consideration only for single fibre systems.

A further possibility is the use of filters which filter out this fluorescence radiation generated by the light conductors. As has already been described with reference to FIG. 2, for example the excitation fibres may thus be combined with a high-pass filter 12 which only allows the excitation radiation 12 to pass but blocks long wavelength fluorescence radiation. The detection fibres which deliver the fluorescence radiation 10 excited at the tooth 4 to the detection device 8 may in contrast be coupled with at least one low-pass filter, which is thus to be arranged in the beam path between the tooth 4 and the detection device 8. This low-pass filter is so configured that it lets through the fluorescence radiation 10 excited at the tooth 4 but not the scattered excitation light which due to its comparatively high intensity in the detection fibres generates a disturbing level of fibre fluorescence radiation. This low-pass filter can be used additionally to the already described spectral fluorescence filter 7 or in place of the spectral filter 7 before the detection device 8 and has a pass band for wavelengths above the actual excitation wavelength, in particular for wavelengths above ca. 800 nm.

Figure 3:
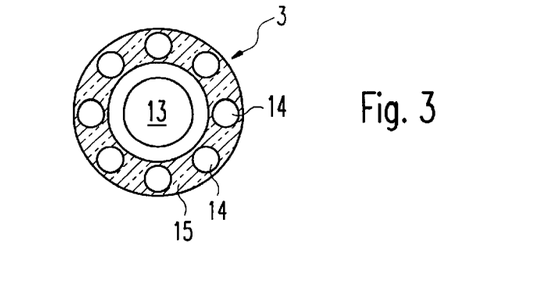
FIG. 3 shows an exemplary cross-sectional view of a light conductor of the device in accordance with the invention shown in FIG. 1 or FIG. 2, FIGS. 4a–4c show various configurations of a light conductor probe of the device in accordance with the invention shown in FIG. 1 or FIG. 2.

FIG. 3 shows a light conductor 3 having a particularly advantageous combination of a non-fluorescing excitation fibre 13 for the transmission of the excitation radiation with a plurality of concentrically arranged detection fibres 14 for the detection and transmission of the fluorescence radiation 10, whereby the detection fibres 14 are provided with the above-described filter or filters which are realized in the case of the exemplary embodiment shown in FIG. 3 by means of a filter glass ring 15.

Figure 4A:
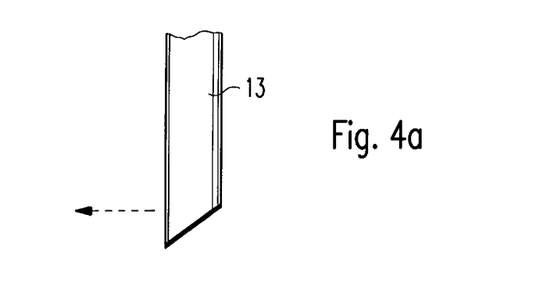
Figure 4B:
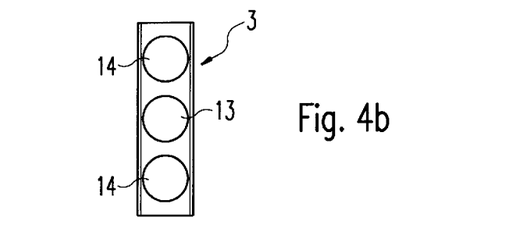
Figure 4C:
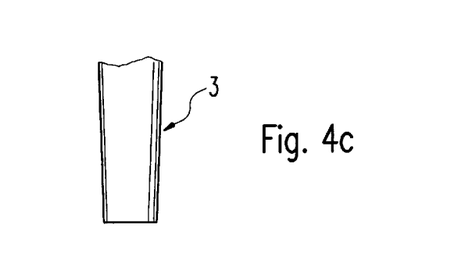

Further investigations have shown that also concretions at tooth roots lead to very clear fluorescence signals and accordingly with the aid of the present invention can be simply detected. In order to be able to use the method in accordance with the invention in therapy monitoring also in parodontology it is important that the probe or the applicator with the light conductor can be introduced into the parodontal pocket. This can for example be ensured in that there is employed as light conductor 3 for the transmission of the excitation radiation 9 solely a single fibre shown in FIG. 4*a*, the end of which is chamfered and made reflective, so that the excitation light emerges laterally from this fibre and can illuminate the root surface in an aimed fashion. Alternatively, as is shown in FIG. 4*b*, the excitation and detection fibres 13 and 14 may be arranged linearly at the tooth or application end of the light conductor 3 in order in this way to make possible an irradiation of the tooth roots and detection of the fluorescence excited there as exactly as possible. FIG. 4*c* finally shows the employment of a light wedge for the transmission of the excitation radiation 9 which likewise can be simply introduced into the parodontal pocket.

The insight upon which the present invention is based, i.e. to increase the detection sensitivity and exactitude in that the fluorescence radiation excited at the tooth is evaluated solely for wavelengths greater than ca. 800 nm, in particular for wavelengths greater than ca. 820 nm, is based upon experimental results which will now be explained in more detail with reference to FIGS. 5 to 10.

Figure 5:
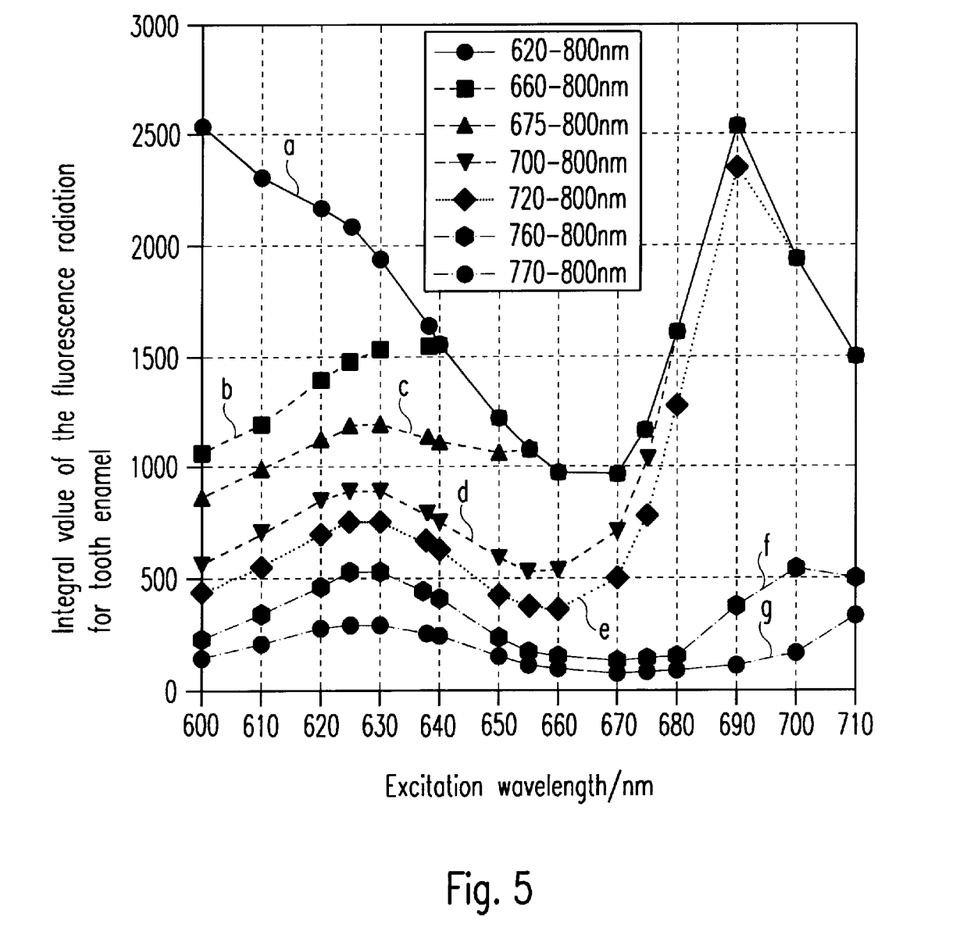
FIG. 5 shows an illustration of the fluorescence radiation in dependence upon the excitation wavelength in the case of healthy tooth enamel, whereby the fluorescence radiation is integrated over different wavelength regions.
Figure 6:
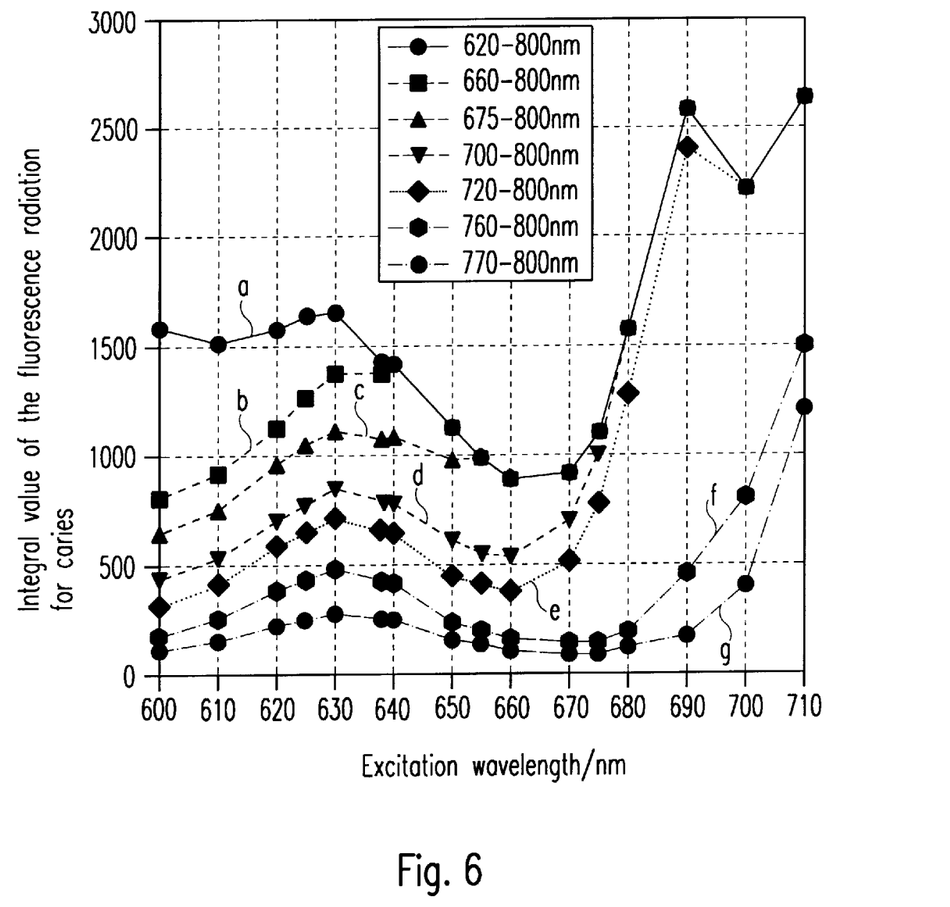
FIG. 6 shows an illustration of the fluorescence radiation in dependence upon the excitation wavelength for a carious tooth region, whereby the fluorescence radiation is integrated for different wavelength regions.

In order to further increase the detection sensitivity, i.e. to increase the difference between the measurement signals from healthy and carious tooth regions, there was measured the excited fluorescence emission spectra for each of three samples of healthy tooth enamel, dentine and caries, whereby this measurement was carried out for in total 16 different excitation wavelengths in the range from 600 nm to 710 nm. The fluorescence emission spectra as such, and their variation with the excitation wavelength, are overall very similar for healthy and carious tissue. In order to determine what possibilities for distinction are offered by detection with different limit wavelengths for the evaluation of the fluorescence radiation, i.e. with different cut-off filters, the intensity of the fluorescence spectra was integrated starting from different wavelengths of the fluorescence radiation up to the fluorescence radiation wavelength 800 nm. The results of these measurements are illustrated in FIGS. 5 and 6, whereby FIG. 5 shows the integral value of the respective fluorescence radiation wavelength range for tooth enamel and FIG. 6 shows the integral value of the respective fluorescence radiation wavelength range for carious tooth regions. Curve a) corresponds to the integral value for the wavelength range of the fluorescence radiation from 620 nm to 800 nm, whilst curve b) corresponds to the fluorescence radiation wavelength range 660 nm to 800 nm. Curve c) is associated with the fluorescence radiation wavelength range 675 nm to 800 nm, whilst curve d) illustrates the fluorescence radiation wavelength range 700 nm to 800 nm. The curve development e) corresponds to the wavelength range 720 nm to 800 nm, the curve f) corresponds to the wavelength range 760 nm to 800 nm and curve g) corresponds to the wavelength range 770 nm to 800 nm of the fluorescence radiation.

Comparison of the diagrams illustrated in FIGS. 5 and 6 shows, in the range of the excitation wavelength between 600 nm and 670 nm known from DE 19541686 A1, for none of the tested integral ranges, any particularly large differences between the fluorescence radiation excited at the tooth enamel and the fluorescence radiation excited at the carious region. Such clear differences first appear with relatively large excitation wavelengths above 680 nm, in particular above 700 nm, whereby clear differences are in particular then to be recognized when the detection range is restricted to long wave fluorescence radiation (c.f. the curve developments f) and g)).

Figure 7:
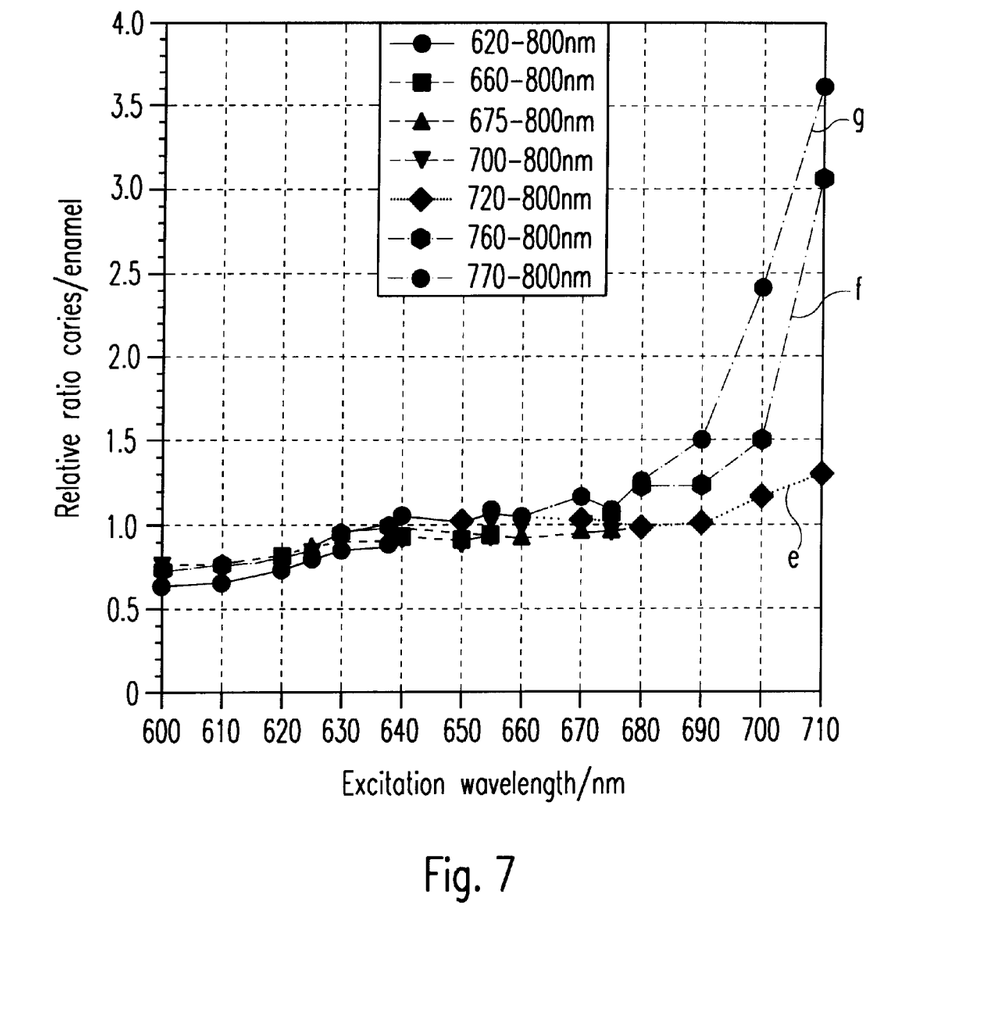
FIG. 7 shows a summarising illustration of the measurement results shown in FIG. 5 and FIG. 6.

The measurement results explained with reference to FIGS. 5 and 6 are summarized in FIG. 7, whereby for the integral ranges of the fluorescence wavelength already shown in FIGS. 5 and 6 in each case the relative ratio of the detected fluorescence radiation for carious tooth regions and the fluorescence radiation excited at tooth enamel is illustrated in dependence upon the excitation wavelength. In particular in FIG. 7 the curve developments f) and g) are again illustrated, which correspond to the curves f) and g) shown in FIGS. 5 and 6 and correspond to an integral detection of the fluorescence radiation excited at the tooth for the fluorescence wavelength range 760 nm to 800 nm and 770 nm to 800 nm. On the basis of FIG. 7 it is clear that the difference between caries and tooth enamel is improved and the quotient of the measurement signals for caries and tooth enamel is greater when only the longer wavelength fluorescence radiation (c.f. curves f) and g)) is used.

On the basis of the above described observations, the investigations were continued for even greater wavelengths in the near infrared range (NIR-range), although here in fact no fluorescence radiation was expected in the biological field.

For this purpose there were carried out some test measurements with a laser diode emitting an excitation wavelength of 780 nm, which with the aid of a high-pass filter was freed of long wavelength background radiation, and a corresponding cut-off filter that is transparent for wavelengths of the fluorescence radiation greater than ca. 850 nm. For purposes of comparison, there was investigated the combination known from DE 19541686 A1 of an excitation wavelength of ca. 655 nm and a spectral filter that is transparent for fluorescence radiation having a wavelength greater than 670 nm. The transmissivities of the filters employed for the measurements are illustrated in FIG. 11, whereby curve a) shows the transmissivity of the cut-off filter having a pass band for wavelengths greater than ca. 850 nm and curve b) shows the transmissivity of the spectral filter having the pass band for wavelengths greater than ca. 670 nm.

Figure 11:
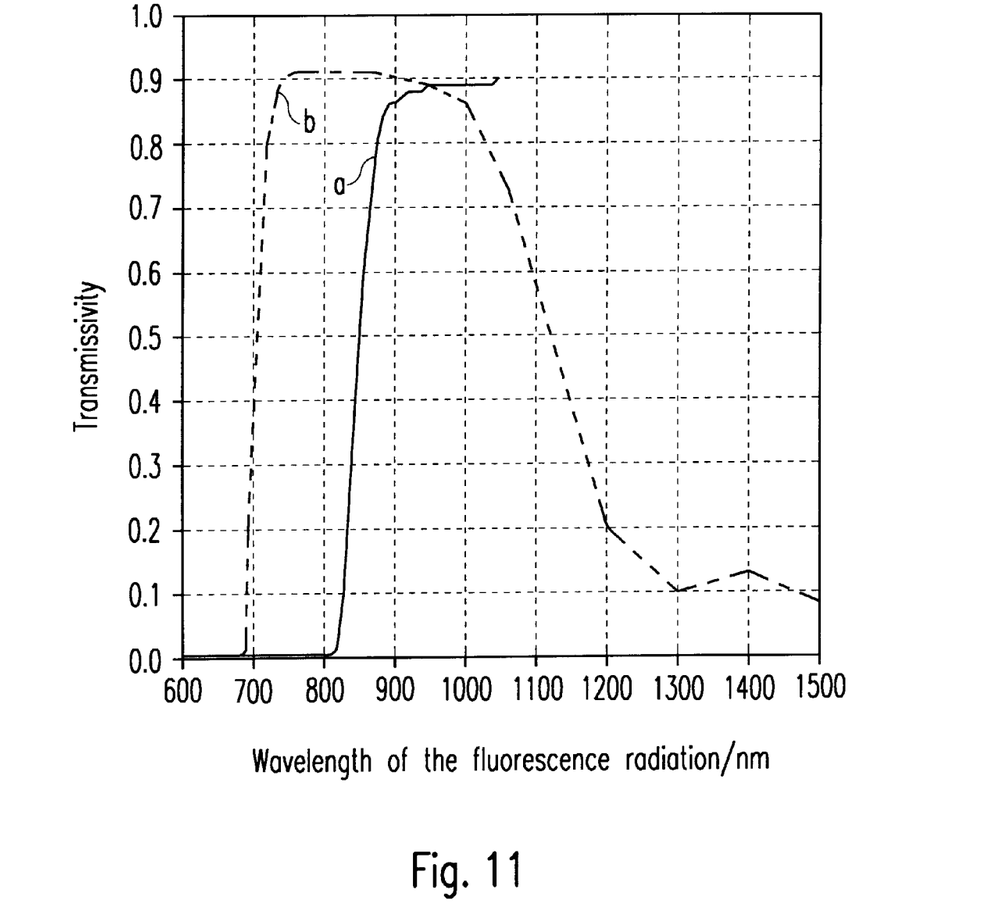
FIG. 11 shows a comparison of the transmissivity of two filters which were employed in investigations.

The results obtained in the course of these investigations confirm that under the above-described conditions, i.e. with an excitation wavelength of ca. 780 nm and a detection of the fluorescence radiation for wavelengths greater than ca. 850 nm (c.f. curve a) in FIG. 11), virtually no fluorescence radiation from healthy tooth enamel or dentine could be detected, whilst in contrast a fluorescence radiation from carious regions could be detected. Although the measurement signals thereby detected are smaller than with the previous procedure, they nonetheless are very clearly distinguishable relative to the very small "noise" signal from the healthy tooth tissue, i.e. there is a large ratio of the measurement signal for carious regions to the measurement signal for healthy tooth regions. By these means, the sensitivity of the detector in the case of hidden caries can be significantly increased. This was checked and confirmed on a range of teeth having approximal caries. It is suspected that with the aid of the above indicated combination of an excitation wavelength of ca. 780 nm with an evaluation of the excited fluorescence radiation for wavelengths greater than 850 nm a fluorophore is detected which is not found in the healthy tooth but which is however contained in caries or in concretions and similar components, and which possibly may correspond to an organic deposit or a product of bacterial metabolism. On the other hand, the spectral investigations lead to the suspicion that primarily alterations to the anorganic tissue framework are detected.

Figure 8:
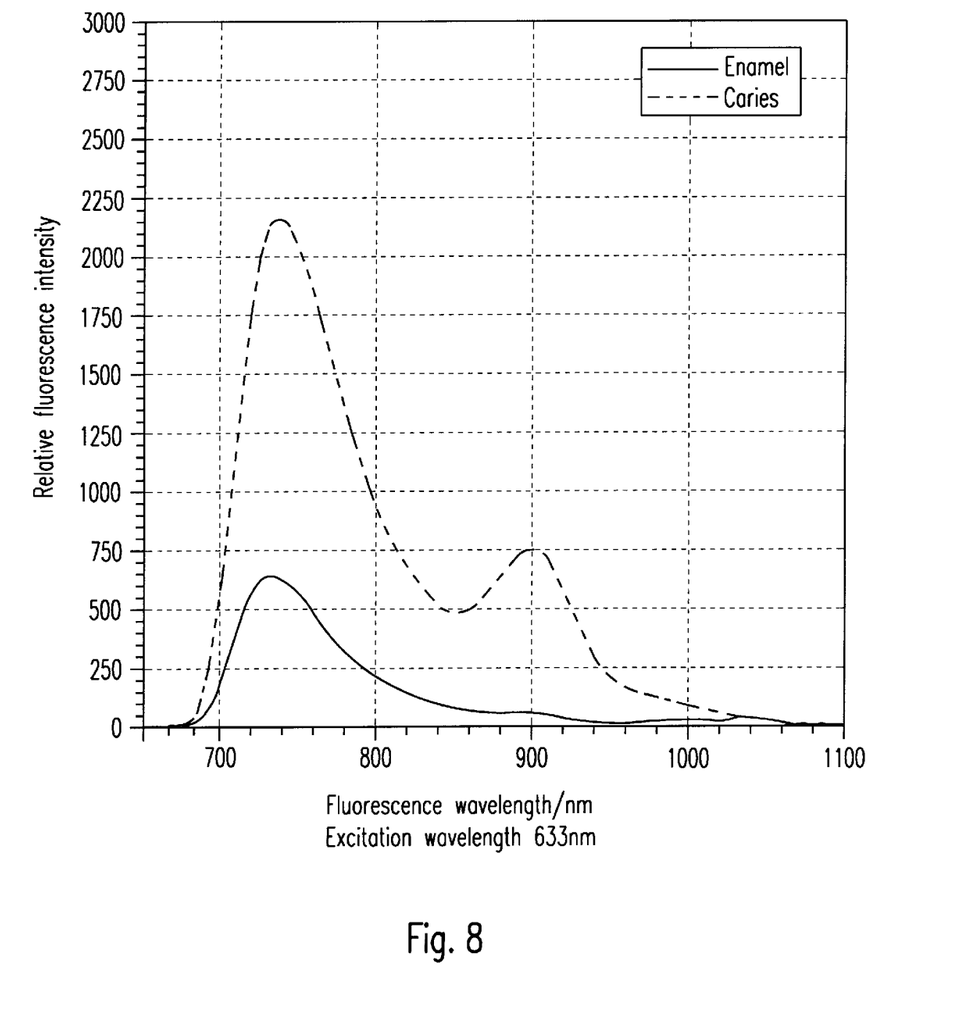
FIG. 8 shows an illustration of the intensity of the fluorescence radiation in dependence upon the fluorescence wavelength, with an excitation wavelength of 633 nm, for a carious tooth region and tooth enamel.
Figure 9:
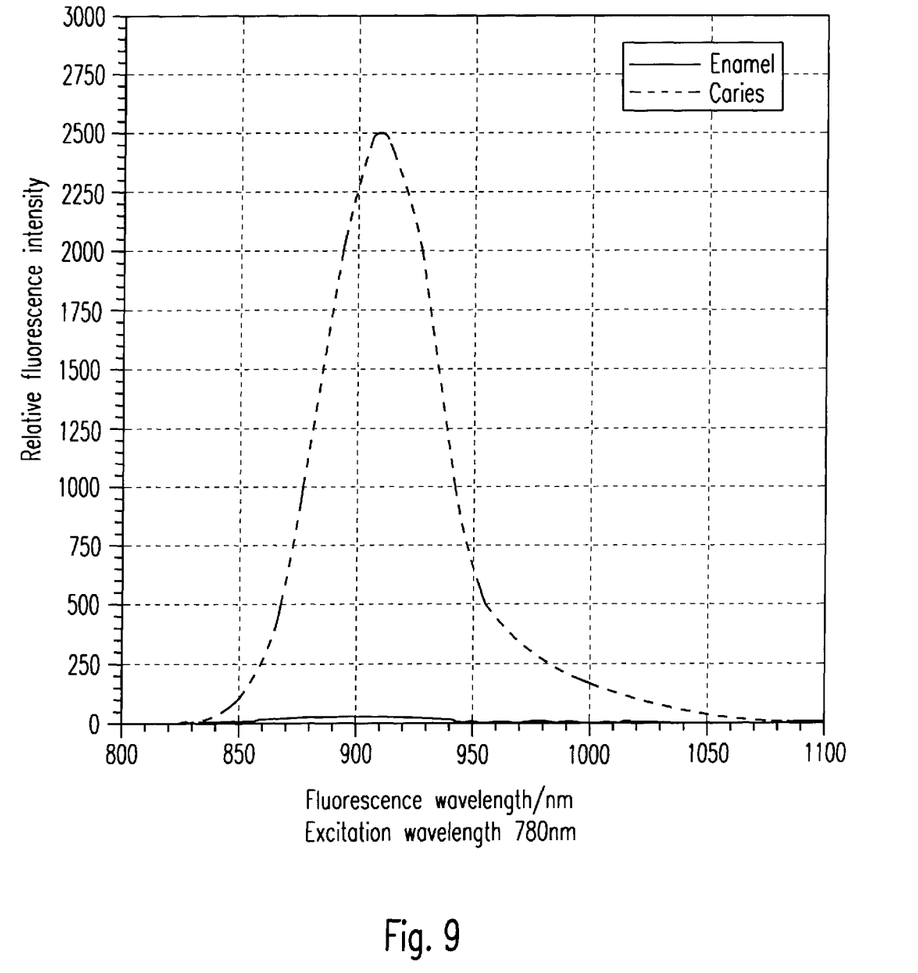
FIG. 9 shows an illustration of the intensity of the fluorescence radiation in dependence upon the fluorescence wavelength, with an excitation wavelength of 780 nm, for a carious tooth region and tooth enamel.

There are illustrated in FIGS. 8 and 9 measurement results for corresponding investigations for an excitation wavelength of 633 nm and 780 nm, whereby in each case the detected fluorescence intensity for carious tooth regions and tooth enamel are indicated in dependence upon the fluorescence wavelength. From FIG. 8 there can be seen from the detected development of the fluorescence radiation for caries a specific emission band around 900 nm, which provides that in the fluorescence wavelength range above 850 nm the fluorescence intensities for caries and tooth enamel are distinguished more clearly than in the overall interval from 700 nm. With the excitation radiation wavelength of 780 nm shown in FIG. 9, the entire fluorescence spectrum in the case of carious tooth regions is formed solely by this single peak, whilst tooth enamel virtually no longer fluoresces, so that the ratio of the fluorescence intensities for caries and tooth enamel for this excitation wavelength can be further increased, thereby to improve the detection accuracy.

Figure 10A:
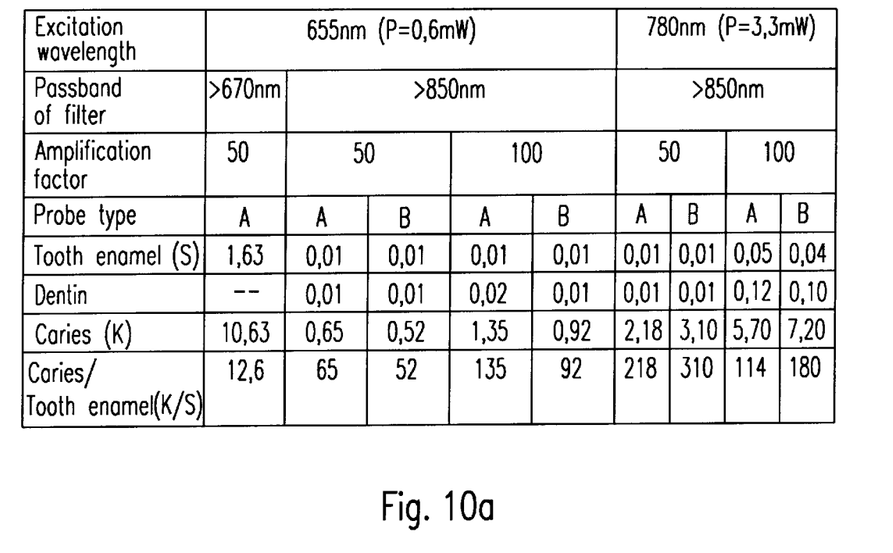
FIGS. 10a and 10b show illustrations of the relationship of the fluorescence radiation of a carious tooth region to the fluorescence radiation of a healthy tooth region for different excitation wavelengths and different evaluated wavelengths of the fluorescence radiation.
Figure 10B:
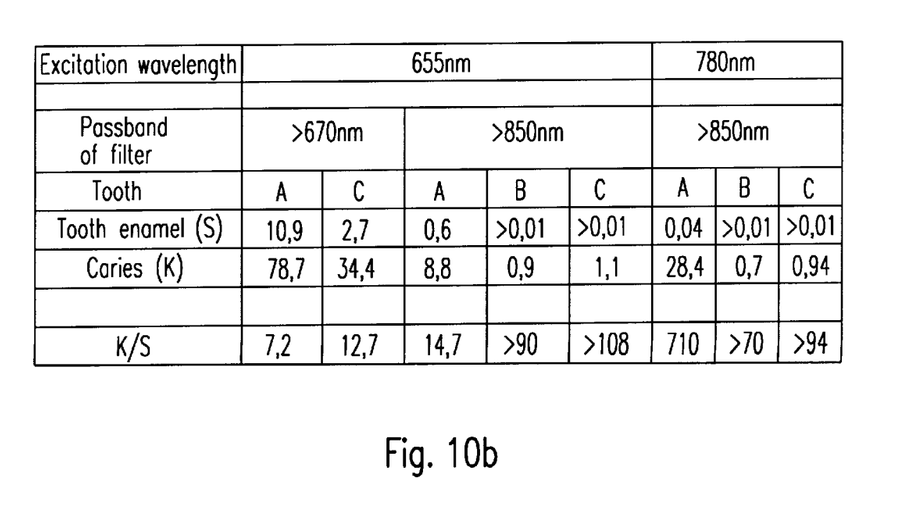

Further information was provided by investigations the results of which are illustrated in FIGS. 10a and 10b.

Thereby, there are illustrated in FIG. 10a, for different excitation wavelengths 655 nm (irradiation power P=0.6 mW) and 780 nm (irradiation power P=3.3 mW), for different limit wavelengths of the spectral filter employed in each case, and for different amplification factors, the intensities of fluorescence radiation thereby detected for healthy tooth enamel, dentine and carious tooth regions. In particular, in FIG. 10a, there are indicated the measurement results for two different kinds of probe (type A and type B). Additionally, in the lowest line of FIG. 10a, there is illustrated for each combination of the respective excitation wavelength with the corresponding spectral filter (cut-off filter), the corresponding amplification factor and the corresponding probe, the ratio of the fluorescence radiation of the carious region to the fluorescence radiation of the tooth enamel region, whereby a greater ratio value corresponds to a greater detection sensitivity, since in this case the measurement signal for carious or infected tooth regions differs significantly from the measurement signal for healthy tooth regions.

If the results illustrated in FIG. 10a for the excitation wavelength 655 nm and 780 nm are compared with one another with in each case the same detection range for fluorescence radiation wavelengths greater than 850 nm, the measurement signals thereby appearing approximately correspond, if the measurement results are normalized for the same irradiation power. This is thus an indication that the above-mentioned fluorophore is approximately similarly strongly excited by both wavelengths. However, if one compares the results illustrated in FIG. 10a with the same excitation wavelength of 655 nm, but for different spectral filters, i.e. for fluorescence radiation wavelengths greater than 670 nm and 850 nm, it is clear that virtually the entire component of the measurement signal obtained with the combination known from DE 19541686 A1 (excitation wavelength 655 nm and evaluation of the fluorescence radiation for wavelengths between 670 nm and 800 nm) originates from the wavelength range between 700 nm and 850 nm, i.e. this component does not originate from the above-mentioned fluorophore which is caries specific to a particular degree.

FIG. 10b shows corresponding measurement results for different teeth A, B and C, whereby the indicated measurement signals are normalized to the power of the excitation radiation and in each case the quotient K/S of the detected fluorescence radiation for caries (K) and tooth enamel (S) is illustrated. One again recognizes that with all teeth A, B and C the detected fluorescence radiations for caries and tooth enamel differ more significantly from one another when the indication or the detection is restricted to long wavelength fluorescence radiation, in particular to fluorescence wavelengths greater than ca. 850 nm, instead of fluorescence wavelengths greater than ca. 670 nm. With the tooth A there is further shown a significant advantage, i.e. a significantly greater quotient K/S for the greater excitation wavelength 780 nm in comparison to the excitation wavelength 650 nm.

In accordance with the measurement results illustrated in FIGS. 5 to 10, there can be attained a particularly sensitive detection of hidden caries, for example in fissures or approximal tooth regions, in accordance with the present invention, if the fluorescence radiation having wavelengths above ca. 800 nm is detected, i.e. the detection range of the fluorescence radiation is restricted to wavelengths greater than ca. 800 nm, since in this wavelength range of the fluorescence radiation caries specific fluorophores and probably also other deposits fluoresce, but not healthy tooth enamel or dentine. Particularly advantageous is the restriction of the detection range to fluorescence wavelengths greater than ca. 850 nm. For the excitation of this fluorescence radiation in principle all wavelengths below 800 nm can be considered. With regard to the optical penetration depth, however, in view of the decrease in scattering with increasing wavelength, an excitation with radiation of as long wavelength as possible is advantageous, so that in particular excitation wavelengths greater than 680 nm, such as e.g. the above indicated excitation wavelength 780 nm, are to be considered.

Since above and below an excitation wavelength clearly different fluorophores or different groups of fluorophores are detected, also the combination of different detection ranges, i.e. different evaluated ranges of the fluorescence radiation wavelength and/or different excitation wavelengths, is advantageous for an improved differentiation and detection (e.g. of decalcifications and lesions having organic deposits or bacterial infection).

What is claimed is:

1. Method for the recognition of caries, plaque, concretions or bacterial infections on teeth, including the steps
    a) irradiation of a tooth (4) to be investigated with an excitation radiation (9) which brings about a fluorescence radiation (10) at the tooth (4), and
    b) detection and evaluation of the fluorescence radiation (10) brought about at the tooth (4) by the excitation radiation (9), in order to recognise caries, plaque or bacterial infection in dependence upon the detected fluorescence radiation (10) at the tooth (4), characterised in that,
in step b) the fluorescence radiation (10) is evaluated for wavelengths greater than ca. 800 nm.

2. Method according to claim 1,
characterised in that,
in step b) the fluorescence radiation (10) is evaluated for wavelengths greater than ca. 850 nm.

3. Method according to claim 1,
characterised in that,
the wavelength of the excitation radiation (9) lies in the range from about 680 nm to about 800 nm.

4. Method according to claim 1,
characterised in that,
in step a) the tooth (4) to be investigated is irradiated with excitation radiations (9) of different wavelengths, and
in that in step b) fluorescence radiations (10) of different wavelengths are detected and evaluated, whereby on the basis of a combination of the individual evaluations of the fluorescence radiations (10) detected in step b) having different wavelengths, caries, plaque, concretions or bacterial infection at the investigated tooth (4) are recognised.

5. Method according to claim 1,
characterised in that,
a long wavelength background radiation is filtered out of the excitation radiation before this irradiates the tooth to be investigated (4).

6. Device for the recognition of caries, plaque, concretions or bacterial infection on teeth, having a light source (1) for the generation of an excitation radiation (9), which is to be directed at a tooth (4) to be investigated and which brings about a fluorescence radiation (10) at the tooth (4), having a detection device (8) for the detection of the fluorescence radiation (10) of the tooth (4), and having spectral filter means (7) arranged before the detection device (8),
characterized in that,
the spectral filter means (7) are so configured to facilitate the through-passage of fluorescence radiation (10) having a wavelength greater than about 800 nm and including a light conductor fiber (13) for the transmission of the excitation radiation (9), the end of which towards the tooth is chamfered and made reflective, so that the excitation radiation (9) emerges laterally from the light conductor fiber (13).

7. Device according to claim 6,
characterised in that,
the spectral filter means (7) are so configured that they let through fluorescence radiation having a wavelength greater than ca. 850 nm.

8. Device according to claim 6,
characterised in that,
the light source (1) generates the excitation radiation (9) with a wavelength in the range from ca. 680 nm to ca. 800 nm.

9. Device according to claim 6,
characterised in that,
the spectral filter means (7) includes a coloured glass cut-off filter and/or a weakly self-fluorescing spectral filter.

10. Device according to claim 6,
characterised in that,
the detection device (8) includes an evaluation device which on the basis of the fluorescence radiation (10) of the tooth (4) detected by means of the detection device (8) determines upon the presence or non-presence of a healthy or diseased tooth region.

11. Device according to claim 6,
characterised in that,
there is provided a light wedge (3) for the irradiation of the tooth (4) with the excitation radiation (9).

12. Device according to claim 6,
characterised in that,
there is provided a common light conductor (3) for the transmission of the excitation radiation (9) and of the fluorescence radiation (10).

13. Device according to claim 12,
characterised in that,
the light conductor (3) has at least one light conductor fibre (13) for the transmission of the excitation radiation (9) and a plurality of concentrically arranged light conductor fibres (14) for the transmission of the fluorescence radiation (10).

14. Device according to claim 13,
characterised in that,
the spectral filter means (7) includes a filter glass ring (15) which is arranged between the concentrically arranged light conductor fibres (14) for the transmission of the fluorescence radiation (10) and the detection device (8).

15. Device according to claim 12,
characterised in that,
between the light source (1) and the end of the common light conductor towards the light source there is provided a beam divider (11) for coupling out the fluorescence radiation (10), so that the detection device (8) can detect the fluorescence radiation (10) coupled out of the common light conductor (3).

16. Device according to claim 12,
characterised in that,
in the common light conductor (3) the at least one light conductor fibre (13) for the transmission of the excitation radiation (9) and at least one light conductor fibre (14) for the transmission of the fluorescence radiation (10) are arranged linearly next to one another at the end of the light conductor (3) towards the tooth.

17. Device according to claim 6,
characterised in that,
amplifier means for the amplification of the fluorescence radiation (10) of the tooth (4) are provided, in order to supply the amplified fluorescence radiation (10) to the detection device (8).

18. Device according to claim 6,
characterised in that,
there are arranged between the light source (1) and the tooth (4) to be investigated further spectral filter means (12) which are so configured that they filter out of the excitation radiation a long wavelength background radiation.

* * * * *